(12) United States Patent
Graether

(10) Patent No.: US 7,891,811 B2
(45) Date of Patent: Feb. 22, 2011

(54) SYSTEM AND METHOD FOR AXIS IDENTIFICATION IN ASTIGMATIC CATARACT SURGERY

(75) Inventor: John M. Graether, Marshalltown, IA (US)

(73) Assignee: OculoCAM, LLC, Marshalltown, IA (US)

( * ) Notice: Subject to any disclaimer, the term of this patent is extended or adjusted under 35 U.S.C. 154(b) by 199 days.

(21) Appl. No.: 12/205,978

(22) Filed: Sep. 8, 2008

(65) Prior Publication Data

US 2010/0060855 A1 Mar. 11, 2010

(51) Int. Cl.
*A61B 3/14* (2006.01)
*A61B 3/10* (2006.01)
*A61B 3/00* (2006.01)

(52) U.S. Cl. .................. 351/206; 351/221; 351/246

(58) Field of Classification Search ......... 351/205–206, 351/210, 221, 200, 246, 212, 214, 247
See application file for complete search history.

(56) References Cited

U.S. PATENT DOCUMENTS

| 5,549,597 A * | 8/1996 | Shimmick et al. | 606/5 |
| 2003/0128334 A1 * | 7/2003 | O'Donnell, Jr. | 351/209 |
| 2006/0262271 A1 * | 11/2006 | Schiabel et al. | 351/212 |

OTHER PUBLICATIONS

ALCON; AcriySof Toric IOL Calculator Online "Lens Recommendation"; webpage printout (page 1 of 1) dated May 30, 2008.

* cited by examiner

*Primary Examiner*—Scott J Sugarman
*Assistant Examiner*—Dawayne A Pinkney

(57) ABSTRACT

A method and system for identifying an astigmatic axis having a camera and light mounted to a slit lamp for taking a photo of a patient's eye. A template having a rotatable dial is set using a schematic diagram. The template is transferred to the photo and the correct axis is marked through slots on the template.

10 Claims, 7 Drawing Sheets

SYSTEM AND METHOD FOR AXIS IDENTIFICATION IN ASTIGMATIC CATARACT SURGERY

BACKGROUND OF THE INVENTION

This invention is directed toward a system and method for identifying the astigmatic axis of the eye during cataract surgery, and more specifically a system and method for accurately placing the toric (astigmatic correcting) intraocular lens implant on the correct axis.

To achieve maximum benefit from the toric lens implant, placement of the lens accurately on the steep axis of the astigmatism must be accomplished. When the patient is made recumbent for surgery, the oblique eye muscles may induce rotation or torsion of the globe such that the relationship to the orbit is altered rendering the true axis of the astigmatism uncertain. Present methods of marking the eye with ink are problematic. Not only is the marking process difficult and time consuming, but also present methods are inherently inaccurate. Therefore, there exists a need in the art for a system and method that addresses these deficiencies.

An objective of the present invention is to provide a system and method that more accurately identifies the axis on which the toric (astigmatic) intraocular lens implant is to be placed.

Another objective of the present invention is to provide a system and method of identifying the axis that is easy to apply and less time consuming for the surgeon.

These and other objectives will be apparent to those skilled in the art based upon the following written description and drawings.

SUMMARY OF THE INVENTION

A method and system of identifying the astigmatic axis includes a camera and light mounted to a moveable carriage of a slit lamp. The camera is positioned, a photo is taken, and the photo transferred to a printer with a display for labeling.

A template having a rotatable dial is placed over a schematic diagram showing the intended axis of the positive (steep) cylinder correction and set so the axis slots on the dial align with the correct axis as shown on the diagram. Once set, the template is transferred to the display or photo and the correct axis is marked through slots on the template.

DETAILED DESCRIPTION OF THE PREFERRED EMBODIMENT

Figure 1:
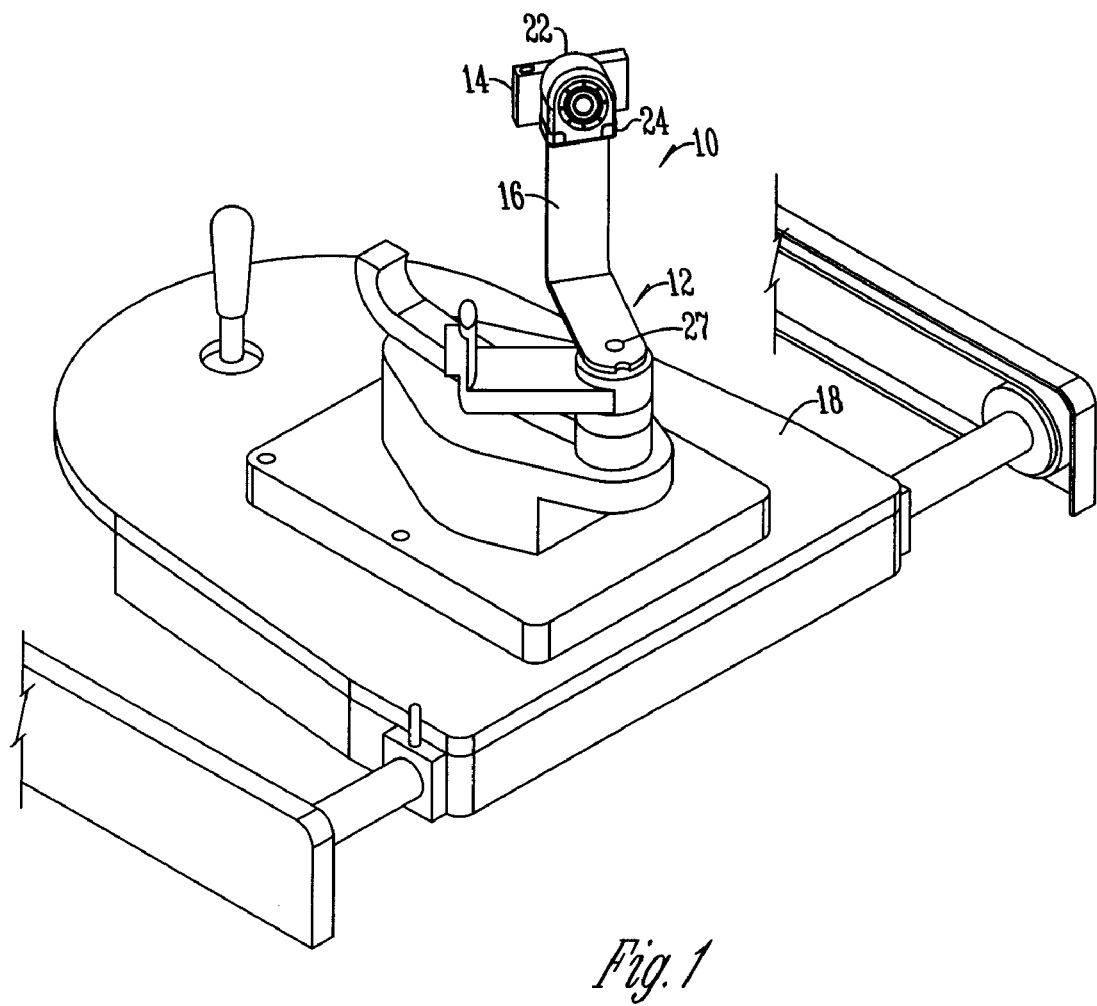
FIG. 1 is a perspective view of a camera and light mounted to a slit lamp.
Figure 1A:
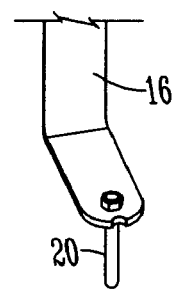
FIG. 1A is a partial perspective view of a bracket.
Figure 2:
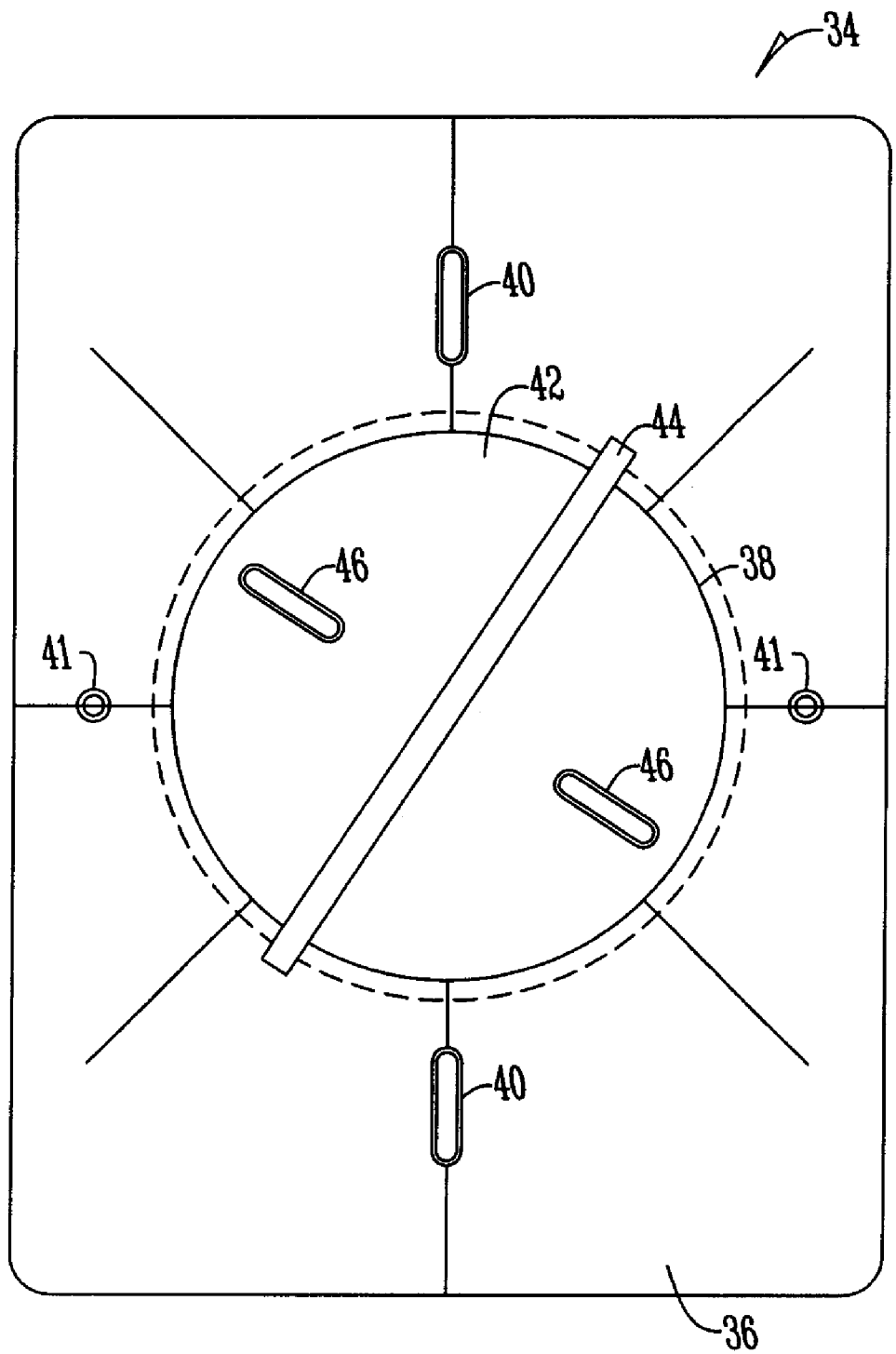
FIG. 2 is a top plan view of a template.
Figure 3:
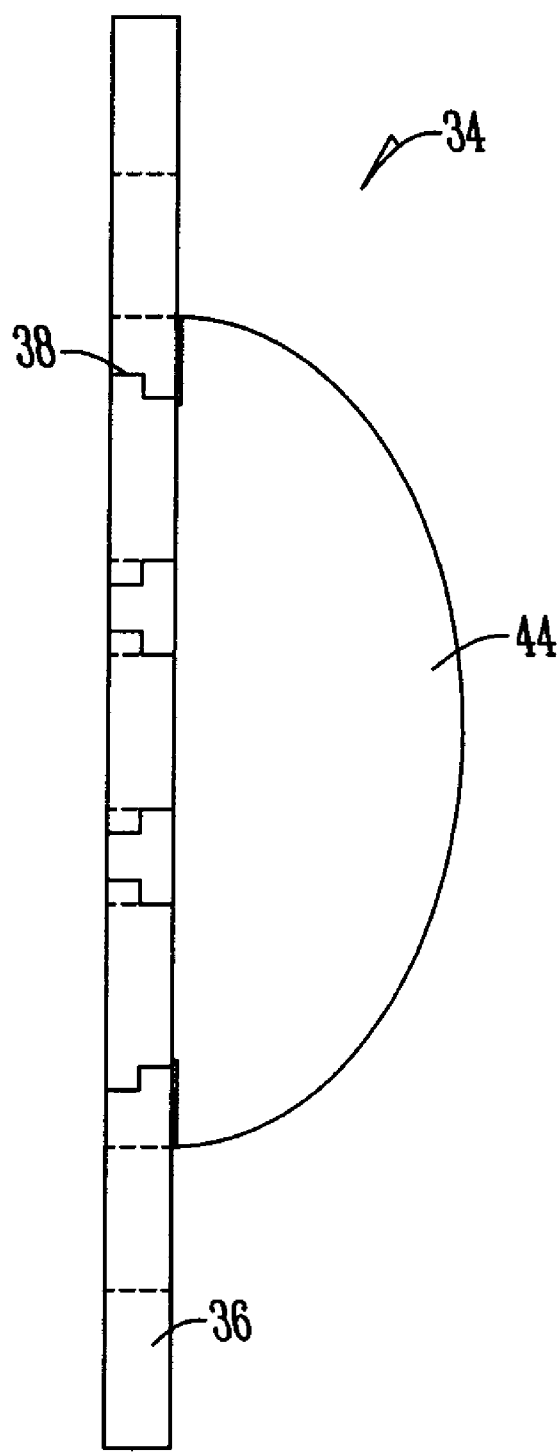
FIG. 3 is a sectional view of a template.
Figure 4:
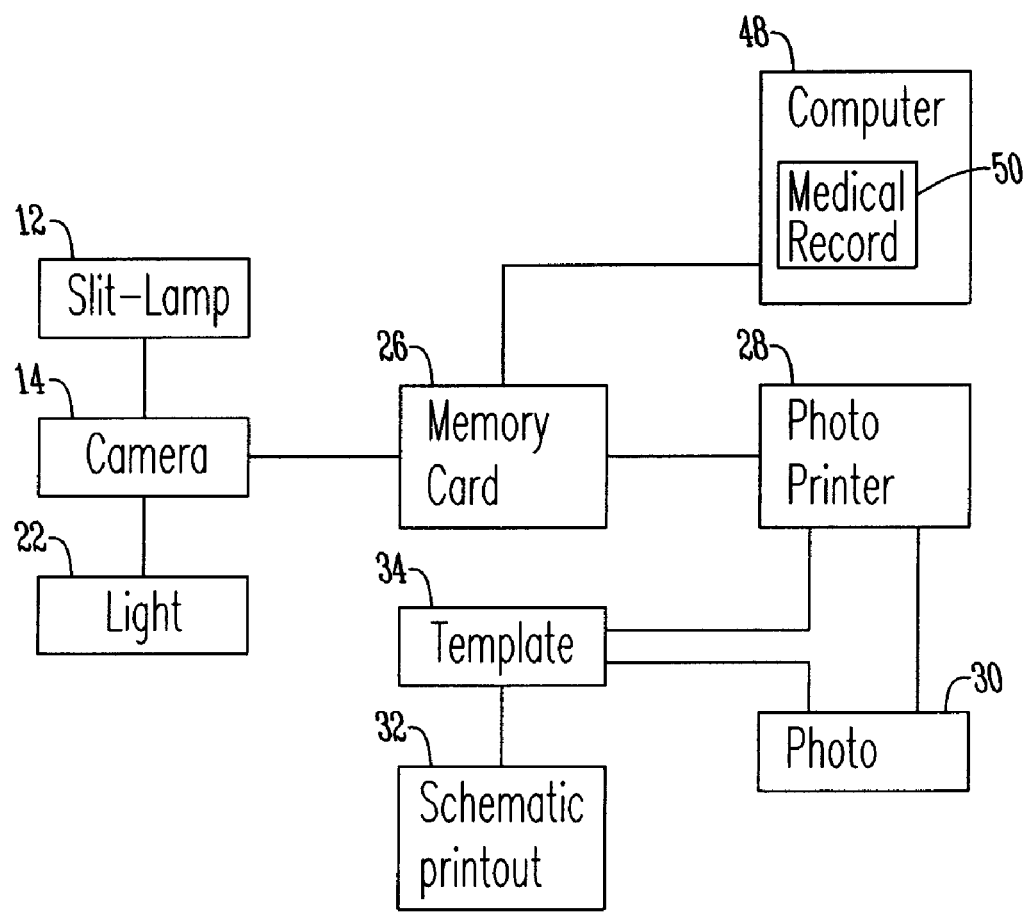
FIG. 4 is a schematic view of the system.
Figure 5:
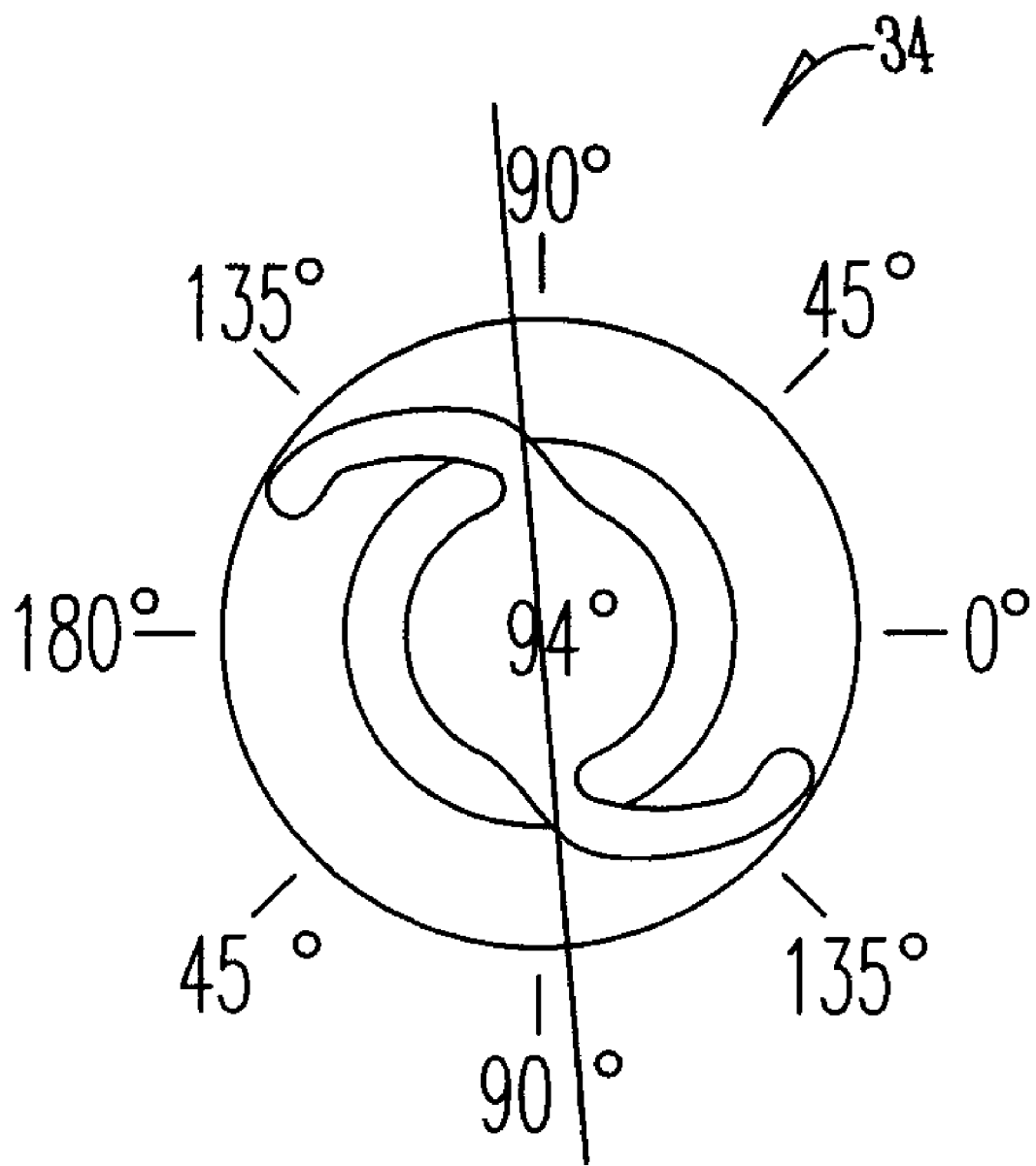
FIG. 5 is a schematic diagram of an astigmatic axis.
Figure 6:
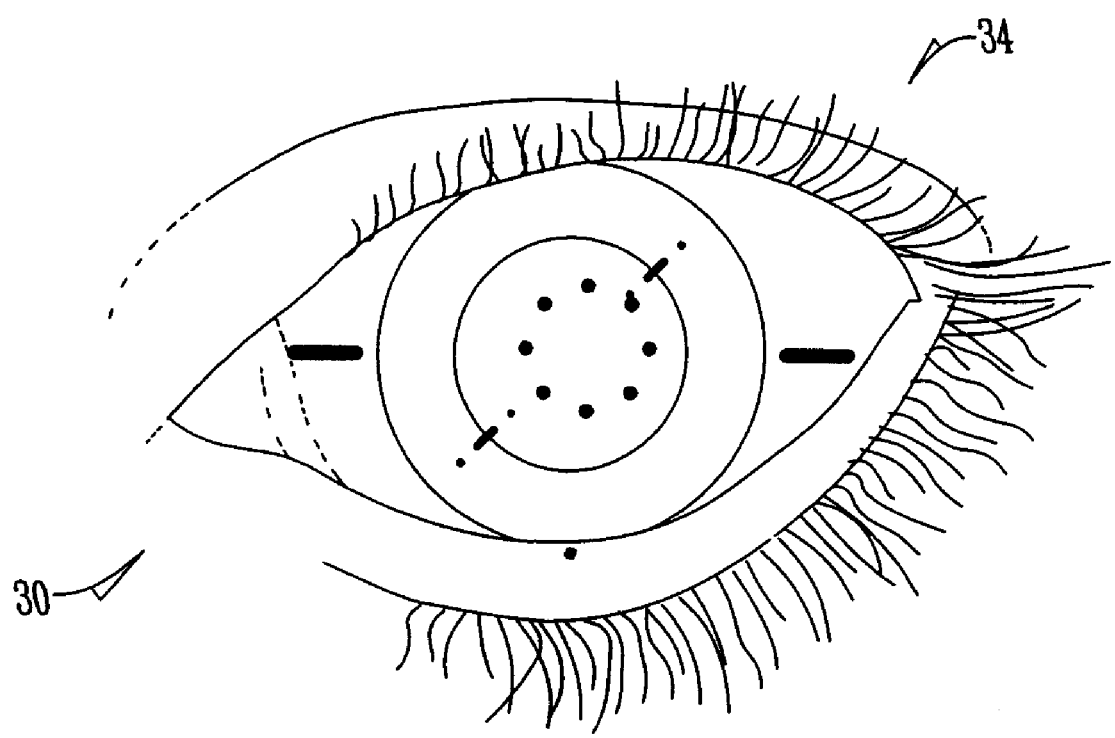
FIG. 6 is a photo of an eye marked with an astigmatic axis.
Figure 7:
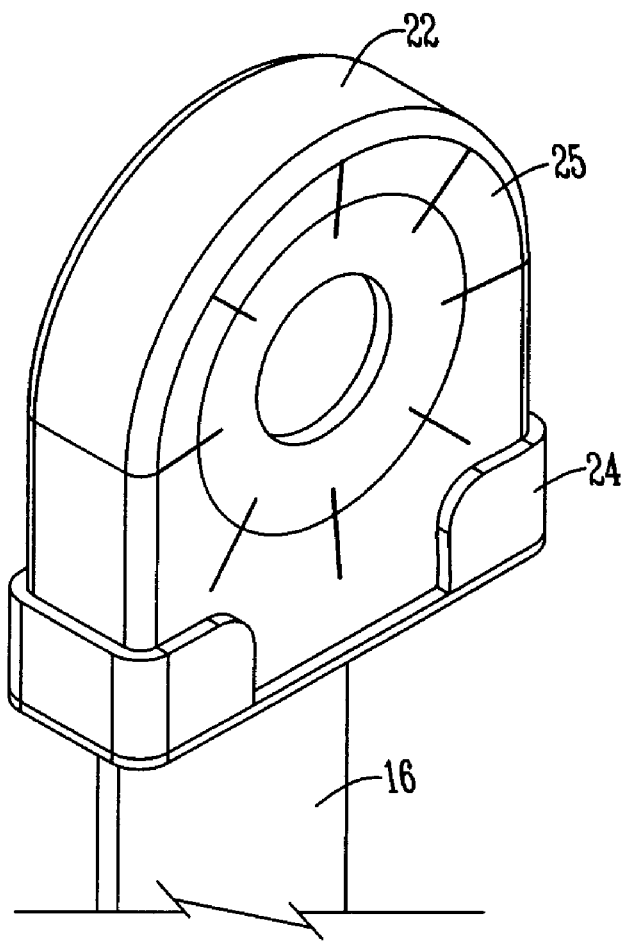
FIG. 7 is a perspective view of a light with a mask.
Figure 8:
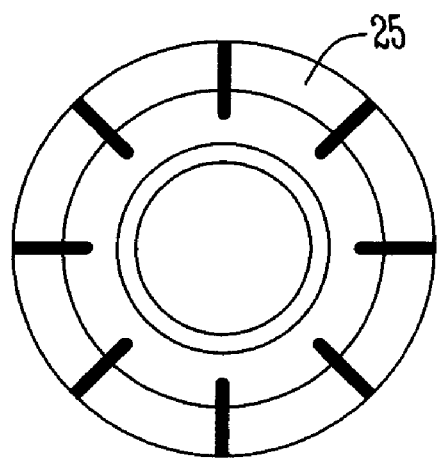
FIG. 8 is a front view of a mask.

Referring to the Figures, the system 10 is designed for use with a conventional Haag-Streit 900 or Haag-Streit 900-type slit lamp 12 or similar device. The system 10 includes a camera 14 that is attached by a bracket 16 to the moveable carriage 18 of the slit lamp 12. The moveable carriage 18 travels on a horizontal track and is elevated by a screw mechanism to position the camera 14 on the correct plane with the patient's head.

The bracket 16 has a post 20 that fits into a central hole in the carriage 18 so that the bracket 16 and camera 14 move with the carriage 18. The camera 14 is mounted to the bracket 16 in any convenient manner such as a tripod screw. The camera 14 is of any type and preferably a simple point-and-shoot, high resolution, digital camera such as Canon PowerShot SD 790 IS having 10 megapixel sensor.

A light 22 is mounted to a support 24 that preferably is mounted to the bracket 16 in conjunction with the camera 14 so that the light 22 moves in tandem with the camera. The light 22 is of any type and preferably is a ring light having eight LEDs arranged in a circle so that there are two lights on the vertical axis, two lights on the horizontal axis and two lights on the 45° and 135° axes such as the Nikon Macro Cool Light SL-1. Alternatively, the light may have a mask 25 applied to create linear streaks rather than points of light on the above four axes. Also, the mask 25 may contain axis lines and concentric circles to produce a Placido's disk effect and identify the principal axes. This pattern will also identify corneal astigmatism or corneal surface irregularities. (A light such as Digi-Slave Mini L-Ring Ultra would be used for the later application.)

In operation, a patient is placed against the slit lamp chin rest and forehead strap in the usual manner to ensure a vertical and stable orientation. The camera 14, that is attached to bracket 16, is mounted to the carriage 18 of the slit lamp 12 by inserting post 20 into the central hole 27 of the carriage 18. The camera 14 is turned on, the flash function turned off, and the camera is set to 'Macro'. The patient's uninvolved eye is patched.

With the light 22 turned on, using the joy-stick of the slit lamp 12, the ring lights, reflected on the cornea of the eye, are aligned in the pupil. The light should be positioned as close to the patient's eye as the anatomy will permit, and the patient is instructed to look to the dark center of the light. Once positioned, the shutter button of the camera is pushed half way to achieve a focus, and then all the way to create an exposure.

A satisfactory exposure is one where the image is in sharp focus, the ring light reflections are centered on the pupil, there is exposure of the limbus at the 6 o'clock position, and there are visible landmarks such as the limbus vessels, pigment, and iris details especially on the horizontal axis and the indicated astigmatic axis.

Once a satisfactory exposure is obtained, the memory card is removed and inserted into a photo printer 28 such as an HP A626 printer. Using the functions of the printer, the photo 30 is selected, cropped, and labeled. In cropping, the photo 30 may be enlarged and/or positioned such that the salient landmarks of the limbus vessels and iris details are shown. This view should include the entire eye from inner to outer canthus. The photo is labeled with the patient's name, the eye (OD or OS) and the date.

The print-out 32 of the toric calculations from the lens manufacturer's computer program includes a schematic diagram showing the correct axis of the positive cylinder correction and gives the axis number in degrees of the compass (i.e., 137 degrees). Using the printer functions, the numerical axis number from the schematic diagram is added to the photo 30 in large red numerals. Once cropping and labeling are completed, the photo is printed.

A template 34 is used to mark the axis on the photo 30. Preferably, the template 34 has a rectangular base 36 with a centrally located circular opening 38. Two slots 40 surround the opening to mark the horizontal axis (at 0 and 180 degrees)

and two small circular openings 41 outside the circular opening 38 marks the vertical axis or 90 degree position. Frictionally received within the opening 38 is a rotational member 42 having an upwardly extending flange or handle 44 and a pair of slots 46 that are on opposite sides of the handle and are linearly aligned.

The template 34 is placed over the schematic print-out 32 such that slots 40 align with the horizontal axis on the print-out 32. The rotational member or dial 42 is turned so that slots 46 are aligned with the indicated astigmatic axis. The template 34 is then transferred to the photo 30 without moving the dial 42 and aligned along the horizontal axis of the photo 30. The dial 42 is centered on the circle of the cornea and the astigmatic axis is marked on the photo 30 through slots 46 in red ink at the corneal periphery. The horizontal axis is also marked on the photo 30 at 0 and 180 degrees in black ink over the conjunctival area near the limbus. Finally, a point mark (black ink dot) is made at the 6 o'clock or 90 degree point through circle 44 at or near the limbus.

In an alternative embodiment, the photo 30 is downloaded into a computer system wherein the schematic diagram 32 is super-imposed over the photo 30. Once aligned, the photo with the schematic markings is printed. This method eliminates the need to transfer the axis orientation to the photo by hand.

Once markings have been made, at the operation the surgeon may rely on the photo to confirm and transfer the axis marks to the patient's eye under the microscope using the various and constant anatomic features shown in the photo as a guide.

Because of the secure positioning of the patient, the firm support of the camera and consistency of the light source, the system 10 also facilitates the creation of high resolution photos of adnexal (lids and surrounding tissue) pathology such as tumors, lid malpositions, inflammatory lesions and the like. The system 10 can also record corneal and conjunctival lesions such as pterygiums, ulcers, foreign bodies or scars, plus iris lesions and cataract. Because of the light reflexes projected on the cornea, the system 10 may be used to access the angle kappa and determine changes in ocular rotation around the visual axis after strabismus surgery. Its ease of use and availability in the standard examination environment make it possible for the doctor to self-record the images assuring that the pathology observed is accurately represented by the photo. The digital photos are readily transferred into an electronic medical record 50 to enhance the quality and accuracy of the record and are available for patient education.

Thus, a system and method for identifying the astigmatic axis has been disclosed that, at the very least, meets all the stated objectives.

What is claimed is:

1. A system for identifying the astigmatic axis, comprising:
   a slit lamp having a movable carriage;
   a camera and light mounted to the moveable carriage for recording a digital photo;
   a schematic diagram showing a correct axis of positive cylinder correction, and
   a template having a rotatable dial and slots for marking the correct axis on the photo.

2. The system of claim 1 wherein the light is a ring light.

3. The system of claim 1 further comprising a printer.

4. The method of claim 1 wherein the step of setting the correct axis comprises rotating a dial of a template so that slots align with the correct axis shown on a schematic diagram.

5. The method of claim 1 wherein the step of setting the correct axis comprises super-imposing a schematic diagram over the photo with a computer system.

6. The method of claim 1 wherein the step of marking comprises the steps of transferring a template to the photo and making marks on the photo through slots in the template.

7. A system for identifying the astigmatic axis, comprising:
   a slit lamp with a moveable carriage;
   a camera and light mounted to the moveable carriage for recording a digital photo; and
   a computer system where a schematic diagram showing a correct axis of positive cylinder correction is super-imposed over the digital photo.

8. The system of claim 7 wherein the light is a ring light.

9. A method for identifying the astigmatic axis, comprising the steps of:
   mounting a camera and a light to a moveable carriage of a slit lamp;
   taking a digital photo of a patient's eye;
   setting a correct axis of positive cylinder correction; and
   marking the photo with the correct axis.

10. A system for photographing the eye, lids and surrounding tissues, comprising:
    a slit lamp having a moveable carriage;
    a camera and light mounted to the moveable carriage;
    a mask attached to the light;
    a computer for storing photographs in medical records; and
    a computer system where a schematic diagram showing a correct axis of positive cylinder correction is superimposed over the digital photo.

* * * * *